(12) United States Patent
Cougard et al.

(10) Patent No.: US 8,475,567 B2
(45) Date of Patent: Jul. 2, 2013

(54) PROCESS FOR SEPARATING PROPANE AND PROPYLENE USING A DISTILLATION COLUMN AND A MEMBRANE SEPARATION COLUMN

(75) Inventors: Nathalie Cougard, Noisy-le-Roi (FR); Arnaud Baudot, Vernaison (FR); Vincent Coupard, Valencin (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 297 days.

(21) Appl. No.: 12/864,762

(22) PCT Filed: Dec. 16, 2008

(86) PCT No.: PCT/FR2008/001746
§ 371 (c)(1),
(2), (4) Date: Oct. 18, 2010

(87) PCT Pub. No.: WO2009/106706
PCT Pub. Date: Sep. 3, 2009

(65) Prior Publication Data
US 2011/0049051 A1 Mar. 3, 2011

(30) Foreign Application Priority Data
Jan. 28, 2008 (FR) ..................... 08 00436

(51) Int. Cl.
*B01D 53/22* (2006.01)
*B01D 59/00* (2006.01)
(52) U.S. Cl.
USPC ................ 95/50; 95/43; 95/45; 96/4; 203/57; 203/68

(58) Field of Classification Search
USPC ........... 210/640; 95/45, 50; 585/818; 204/57, 204/68, 71, 78, 98; 203/57, 68, 71, 78, 98
See application file for complete search history.

(56) References Cited

U.S. PATENT DOCUMENTS

| | | | | |
|---|---|---|---|---|
| 5,131,928 A * | 7/1992 | Blackman et al. | ................... | 96/5 |
| 5,837,032 A * | 11/1998 | Moll et al. | ......................... | 95/45 |
| 6,316,684 B1 * | 11/2001 | Pinnau et al. | ................. | 585/818 |
| 6,361,582 B1 * | 3/2002 | Pinnau et al. | ..................... | 95/45 |
| 6,414,202 B1 * | 7/2002 | Baker et al. | .................... | 568/895 |
| 6,830,691 B2 * | 12/2004 | Colling et al. | ............... | 210/641 |
| 7,070,694 B2 * | 7/2006 | Colling et al. | ................ | 210/640 |
| 7,250,545 B2 * | 7/2007 | Roman et al. | ................. | 585/818 |
| 7,497,876 B2 * | 3/2009 | Tuke et al. | .................... | 623/23.5 |
| 7,875,758 B2 * | 1/2011 | Sanders et al. | ............... | 585/818 |
| 2003/0233934 A1 | 12/2003 | Wijmans et al. | | |

(Continued)

FOREIGN PATENT DOCUMENTS
WO WO 2008/084415 A2 7/2008

OTHER PUBLICATIONS
International Search Report of PCT/FR2008/001746 (Jul. 31, 2009).

*Primary Examiner* — Ana Fortuna
(74) *Attorney, Agent, or Firm* — Millen, White, Zelano & Branigan, P.C.

(57) ABSTRACT

Process for separating propane and propylene using a distillation column and at least one membrane separation unit constituted by one or more modules operating in series, said membrane separation unit being placed either upstream, or downstream, or upstream and downstream of the distillation column.

7 Claims, 5 Drawing Sheets

U.S. PATENT DOCUMENTS

| | | |
|---|---|---|
| 2004/0000513 A1 | 1/2004 | Colling et al. |
| 2004/0173529 A1 | 9/2004 | Da Costa et al. |
| 2004/0182786 A1 | 9/2004 | Colling et al. |
| 2006/0266213 A1* | 11/2006 | Riu et al. ............... 95/50 |
| 2008/0167312 A1* | 7/2008 | Gant et al. ............. 514/239.5 |
| 2008/0167512 A1 | 7/2008 | Sanders et al. |
| 2011/0049051 A1* | 3/2011 | Cougard et al. ............. 210/640 |
| 2011/0077446 A1* | 3/2011 | Shanbhag et al. ............. 585/818 |
| 2011/0114547 A1* | 5/2011 | Sanders et al. ............. 210/180 |
| 2011/0130611 A1* | 6/2011 | Gonzalez et al. ............. 585/818 |

* cited by examiner

Figure 4 bis

Figure 5

Figure 5 bis

Figure 6

Figure 6 bis

PROCESS FOR SEPARATING PROPANE AND PROPYLENE USING A DISTILLATION COLUMN AND A MEMBRANE SEPARATION COLUMN

This application is a 371 of PCT/FR2008/001746, file on Dec. 16, 2008; which claims priority of application France 0800436, filed on Jan. 28, 2008.

FIELD OF THE INVENTION

In an economic context marked by a growing demand for high-purity propylene (i.e. more than 99.5 mol. % propylene), which can be used in polymerization processes, it is necessary either to develop new propylene production means or to improve the existing solutions.

The present invention can be considered as an improvement of the existing processes based on distillation alone, using a combination of membrane separation units and distillation columns which we call a "hybrid" process in the remainder of the text.

One of the limiting stages of "hybrid" processes resides in the separation of the propane and the propylene by the distillation column. In fact, this column is designed for a certain capacity and generally constitutes the bottleneck among existing fractionation units in refineries.

In fact, distillation columns for the separation of propane and propylene generally have more than 150 theoretical plates and operate with very high reflux rates (generally comprised between 10 and 15), which directly results in very high energy consumption levels.

Apart from the economic aspect it is important to also note the environmental aspect of the $CO_2$ emissions produced by said columns.

Much importance, in both economic and environmental terms, is thus currently attached to the improvement of the separation of propane and propylene.

The present invention describes a process making it possible to reduce the energy cost of propylene/propane separation, and to reduce or shift to higher values the flooding limit of the currently installed distillation columns.

The process which is the subject of the present invention is based on a coupling of the membrane separation units with the distillation column or columns allowing the separation of propane and propylene, as well as on the choice of operating conditions of said membrane separation units which makes it possible to reduce the permeate-recompression costs.

EXAMINATION OF THE PRIOR ART

Membrane techniques are often considered an alternative in the separation of olefins/paraffins combinations. Membrane separations make it possible to significantly reduce the operating costs compared with the distillation conventionally used.

Separation membranes are already used for certain industrial applications. Among these there can be mentioned:

pervaporation membrane separation, in particular in the field of solvent dehydration. This technique is used in particular for the purification of ethanol (distillation—pervaporation coupling), of isopropyl alcohol, acetone and acetic acid. Pervaporation is also used in the elimination of volatile organic compounds from aqueous effluents. The use of hydrophobic rubber membranes makes it possible to eliminate traces of organic components from water in this case, the separation is based on the differences in solubilities between the liquid feedstock and the membrane material, it is therefore very effective for compounds such as chloroform and aromatic hydrocarbons. Finally, pervaporation is also used for the separation of organic mixtures. In this particular case pervaporation can optionally be substituted for (or combined with) distillation. It can be used in particular within the framework of the production of fuel-grade ether.

Within the framework of olefins/paraffins separation, it has been demonstrated that separation membranes were not economically viable when used alone "Separation of Ethylene from Ethane using Perfluorosulfonic Acid Ion Exchange Membranes" (by Sungpet et al., ACS Symposium Series "Chemical Separation with Liquid Membranes" 270-285, 1996. [2].

The work of Petterson et al. (Separation Technology 6, (1996), 175-187) focuses on the coupling of separation membrane with a distillation column. The reference distillation column, also called a "splitter", is constituted by 152 theoretical plates and operates initially with a reflux of 24.1 in order to separate the propylene/propane until a purity of 99.5% is obtained. As regards the membrane material, the authors mention the use of a Nafion type material with fixed selectivity. In their work, the membranes (operating with gas permeation) are essentially positioned in parallel with the column, they are supplied with a flow at the pressure of the column (17.5 bar), the permeate being at 3.5 bar, which requires the use of a compressor to reinject the flow into the column. The authors affirm that an increased treatment capacity is obtained thanks to the addition of membrane, as well as a possible reduction in internal transport, and in the reflux from the column. The economic evaluation has not been completed, the costs of recompression of the permeate recycled in the column not having been taken into account.

Kookos, in Industrial and Engineering Chemistry Research 42 (2003) 1731-1738, also carried out research into this subject. His work essentially related to membrane configurations (operating with gas permeation) in parallel with the distillation column. The process described by Kookos treats a 70/30 mol. % propylene/propane feedstock and relates to specifications with 99 mol. % propylene at the top of the column. This study is based on a carbon-type membrane having a permeability of 390 barrer for a propylene/propane selectivity of 18.4. The permeability/selectivity combination is therefore very high, but the carbon-type membrane is very fragile. The authors envisage the economic aspect in the case of the construction of a new unit, but not with a view to debottlenecking. Moreover, due to the operating conditions described (relatively low pressure in the permeate) the process uses a compressor to reinject the permeate in gaseous phase into the column.

US patent 2004/0173529 A1 describes several separation systems combining separation membranes with a distillation column. The different configurations envisaged (upstream and downstream of the membrane) in the cited patent comprise compressors, involving significant investment costs. These compressors are in fact necessary to compress the flow of the permeate which is at atmospheric pressure, even under a vacuum.

The examples used in this patent illustrate a distillation column with 58 theoretical plates operating with a reflux rate of 53 in order to obtain a 99 moi % propylene at the outlet. This reflux rate is much greater than the values encountered industrially. Moreover, the process described in the cited patent is intended for the purification of the propylene obtained by dehydrogenation of the propane, which is not the case in the present invention, U.S. Pat. No. 6,899,743 B2 describes a hybrid process involving a combination of membranes and a dephlegmator. This process makes it possible to achieve separations which are four to six times more effective than a partial simple condensation. This process can be used in different fields such as the separation of an azeotrope, the improvement in performance of a membrane alone in the case of a single-phase feedstock intended or not intended to be injected into a distillation column. This patent essentially deals with the effectiveness of the permselective membrane. The membranes in question are effective in the separation of mixtures of aromatic/aliphatic compounds, azeotropes (in particular mixtures containing light alcohols), mixtures of light hydrocarbon isomers and also light olefins/paraffins hydrocarbons (in particular propylene/propane). The material described ensures a permeability of 40 to 50 GPU (approximately 40 to 50 barrer) for a selective membrane thickness of 1 µm and for an average propylene selectivity relative to propane of 4.5.

In this patent, the authors do not explain the targeted operating conditions. The patent does however state that the permeate is maintained under a vacuum by means of a vacuum pump. The process of the cited patent is different from the present invention in particularly due to the fact that the authors add a dephlegmation stage.

Finally, U.S. Pat. No. 7,070,694 B2 also deals with the integration of "perm-selective" membranes into processes for the separation of organic mixtures by distillation. The performances of the processes were evaluated with membranes having a very strong propylene/propane selectivity (approximately 15) and reduced permeability (2 barrer).

These membranes are used in gas permeation and placed at the top of the distillation column or in parallel. The low pressure at the membrane outlet (approximately 40 psia, or 2.75 bar according to the examples) makes it necessary to compress the permeate in order to recover the PG propylene (99.5 mol. % propylene) resulting in probably high recompression costs. Generally, the membrane separation processes described in the literature require a permeate at low pressure (close to atmospheric pressure, even under vacuum) in order to benefit from the greatest possible difference in pressure on either side of the membrane. In these cases, in order to be able to reinject the permeate into the process, it is necessary either to condense it with a refrigerating unit (a very expensive operation in terms of investment and operating costs), or to recompress it (also a very expensive operation).

The present process, unlike the processes described in the prior art, uses a partial propylene pressure in the feedstock which is close to the critical point upstream, in order then to have available a flow of permeate at a pressure such that it can be directly and easily reinjected into the propylene/propane separation distillation column at a pressure close to the pressure of the injection plate of said column. If the pressure of the permeate is equal to that of the injection plate, the permeate can be injected directly in gas phase into the column.

If the pressure of the permeate is only close to (for example plus or minus 3 bar) that of the reinjection plate, a condensation will then be carried out (with water or air) then a re-establishment of pressure by pump, a very inexpensive process.

One of the significant advantages of using the membrane module at pressures and temperatures higher than those used according to the prior art lies in the fact that the present process does not require compression of the gas permeate, unlike the other processes described in the prior art.

Overall, the process according to the invention is therefore clearly more economical than the processes of the prior art.

Moreover, the reduction in the energy cost of the distillation column is also accompanied by a favourable impact on the environment due to the reduction in gas emissions due to the greenhouse effect, in particular $CO_2$.

SUMMARY DESCRIPTION OF THE FIGURES AND DEFINITION OF TERMS

In the remainder of the text, the term "membrane module" is used to denote the membrane alone (assembly of hollow fibres covered with polymer and grouped together in the same calender), and the term "membrane separation unit" to denote a group of membrane modules, said group being able to comprise one, two, three or more membrane modules operating in series as well as the apparatus necessary for the satisfactory operation of said unit (exchanger, pump).

The term "pervaporation conditions" is used when the pressure recorded at the inlet to each membrane module on the upstream surface of the module (in contact with the feedstock to be separated) is comprised between 20 bar and 47 bar (1 bar=$10^5$ pascal), and when the feedstock temperature is comprised between 50° C. and 92° C.

The term "supercritical conditions" is used when the pressure recorded at the inlet to each membrane module on the upstream surface of the module (in contact with the feedstock to be separated) is comprised between 47 bar and 100 bar (1 bar=$10^5$ pascal), and when the feedstock temperature is comprised between 92° C. and 200° C.

FIG. 4*bis* shows a membrane separation unit, having a single membrane module, and operating under pervaporation conditions with a pressure of the permeate equal to (or very close to) the pressure of the plate reintroducing into the column.

FIG. 5*bis* shows a membrane separation unit, having two membrane modules, operating in series and under pervaporation conditions with a pressure of the permeate equal to (or very close to) the pressure of the plate reintroducing into the column.

FIG. 6*bis* shows a membrane separation unit, having two membrane modules, operating in series and under supercritical conditions with a pressure of the permeate equal to (or very close to) the pressure of the plate reintroducing into the column.

SUMMARY DESCRIPTION OF THE INVENTION

The present invention can be defined as a process for separating propane and propylene using a distillation column and at least one membrane separation unit constituted by several membrane modules operating in series, said membrane separation unit being placed either downstream or upstream, or downstream and upstream of the distillation column, said membrane separation unit or units operating with polymer membranes having a permeability greater than 0.1 barrer and propylene/propane selectivity greater than 5, either under the following pervaporation conditions, recorded at the inlet to each membrane module: 20 bar<pressure<47 bar and 50° C.<temperature<92° C.

or under the following supercritical conditions, recorded at the inlet to each membrane module: 47<pressure<100 bar and 92° C.<temperature<200° C.

When the process according to the invention operates under pervaporation conditions recorded at the inlet to each membrane module (feedstock pressure comprised between 20 and 47 bar and feedstock temperature between 20° C. and 92° C.), the said separation unit or units operate with a difference in pressure such that the permeate is at a pressure of 10 bar minimum.

In this case, the permeate can be:
a) reinjected directly into the column in vapour phase or
b) directly valorized as high-purity propylene.

Under pervaporation operating conditions, and when the pressure of the permeate is equal to or greater than the pressure in the column, the latter can be reintroduced directly into said column, optionally subject to a pressure reduction or condensation (case b).

When the process operates under supercritical conditions recorded at the inlet to each membrane module (feedstock pressure comprised between 47 and 100 bar, and feedstock temperature between 92° C. and 200° C.), the said separation unit or units operate with a difference in pressure such that the permeate is at a pressure of 10 bar minimum.

In this case, the permeate can be:
a) reinjected directly into the column in vapour phase
b) condensed, repumped then reintroduced in liquid phase into the column.
c) valorized as high-purity propylene which can be used in polymerization processes.

Under supercritical operating conditions, and when the pressure of the permeate is greater than or equal to the pressure in the column, the latter can be reintroduced directly into the column, optionally subject to a pressure reduction or condensation (case c).

DETAILED DESCRIPTION OF THE INVENTION

The present invention is a process for separating propane and propylene using a distillation column and at least one membrane separation unit placed downstream, upstream or also downstream and upstream of said column, said process making it possible to reduce the feedstock of the propylene/propane distillation column, without adding a compressor, which is an essential point in the economy of the process.

The process can optionally utilize several distillation columns, the present invention being applicable to one or more of these columns.

Generally, i.e. for all the configurations corresponding to the process according to the invention, the flow of feedstock to be treated is a $C_3$ refinery cut. This flow contains for the most part propane and propylene.

This flow can also contain impurities such as COS, H2S, mercaptans and dienes. Generally, the propylene content of the feedstock to be treated is 60% by weight minimum.

The process according to the invention can for example be used within the framework of the debottlenecking of an FCC (fluidized-bed catalytic cracking) gas plant. In fact the propylene/propane separation column or columns very often constitute a bottleneck in propylene production.

The integration of membrane separation units upstream or downstream, or upstream and down stream of the distillation column increases the treatment capacity of said column by approximately 30%, as shown in the example forming part of the present application.

These membrane separation units, placed according to different configurations around the propylene/propane distillation column, make it possible to concentrate propylene in the flow passing through the membrane, called the permeate, and consequently to deplete propylene in the residual flow called the retentate. These units can generally operate with a flow of feedstock containing a minimum of 60% by mass propylene. In the case of separation units where the permeate is reintroduced into the column (upstream or downstream) the feedstock preferably contains 70% by mass propylene and in the case of a separation unit situated downstream of the distillation column, a feedstock containing a minimum of 90% by mass propylene will preferably be used.

The transport of the species to be separated through the membrane is ensured by keeping the partial pressure in the permeate lower than in the retentate. This low partial pressure of the permeate can be ensured by various means such as the condensation of the permeate. With a view to achieving the desired level of pressure in the permeate within the framework of this invention, the condensation of the flow of the permeate constitutes the most common option. Nevertheless, any other solution making it possible to achieve a low level of pressure of the permeate remains within the scope of the present invention.

The two flows of retentate and of permeate are then reinjected into the propylene/propane distillation column at levels of said column which preferably best correspond to the compositions of said retentate and permeate.

Some of the process diagrams according to the present invention are based on the pervaporation technique. The motive force involved in pervaporation arises from the difference in starting and partial other pressure of the membrane. The flows enter the membrane in the liquid state, are evaporated through the membrane wall and exit in the gas state.

The effectiveness of the membranes is defined in terms of selectivity (ratio of the propylene permeability to that of propane) and permeability (characteristic of the membrane defining the diffusivity of the feedstock to be treated through said membrane).

The membrane modules involved in the membrane separation units of the process according to the invention operate on the principle of pervaporation or gas permeation, for temperature and pressure conditions covering a wide field of use. Typically between 20° C. and +200° C. and preferably between 50° C. and 100° C., for feedstock pressures comprised between 20 bar absolute and 100 bar (1 bar=$10^5$ pascal).

The polymer constituting the membrane is of organic type. The latter has a propylene/propane selectivity of at least 5 and preferably at least 10, and a minimum permeability of 0.1 barrer (selectivity and permeability being related to to the propylene/propane combination). The barrer is a unit specific to the technologies of separation by diffusion through dense films, and equivalent to $10^{-10}$ $Ncm^3$ $cm/cm^2$ $m\cdot_{Hg}^{1}\cdot s^{-1}$ In the case where the operating conditions of the membrane separation units are chosen below the critical point (P<47 bar and T<92° C.), the permeate pressure is chosen equal or close to the pressure of the distillation column, i.e. greater than or equal to 15 bar. The temperature fixed in the membrane module is therefore chosen such that a) the feedstock is in liquid phase, b) the partial pressure of the propylene in the feedstock is always greater than the partial pressure of the propylene in the permeate, and c) the permeate is always in gas phase.

Figure 5:
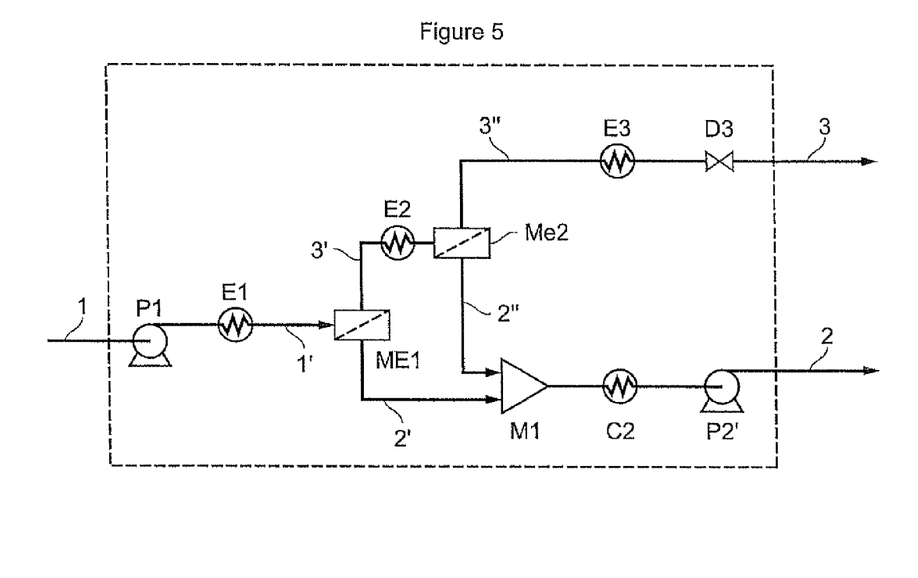
FIG. 5 shows a membrane separation unit, having two membrane modules, operating in series and under pervaporation conditions.

As the flow of feedstock must be reheated in order to allow the evaporation of the permeate during the pervaporation stage, this results in the presence of an intermediate reheater between each membrane module, as shown in FIGS. 5 and 5*bis*.

Figure 6:
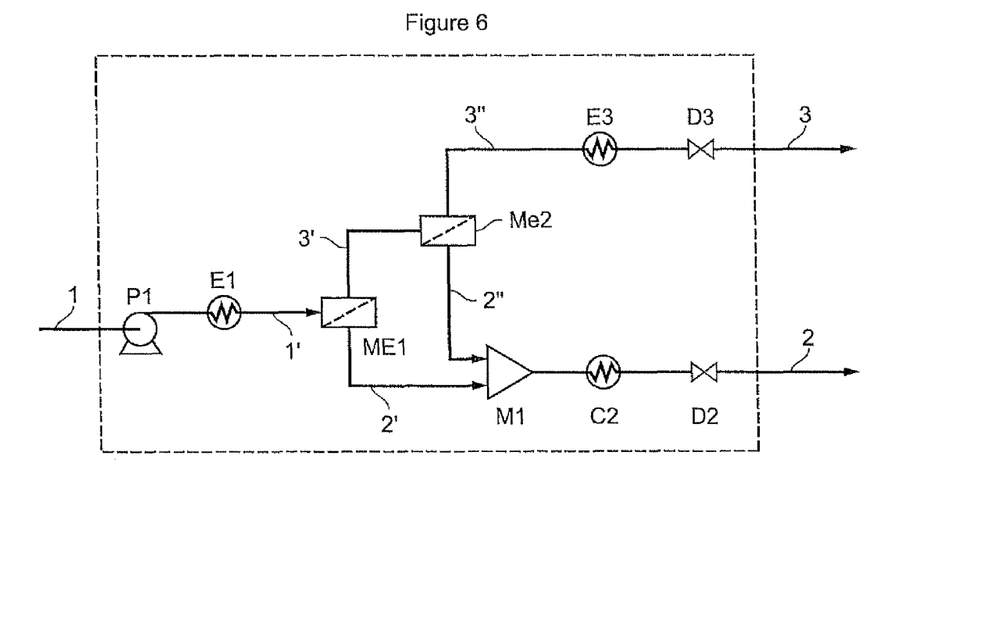
FIG. 6 shows a membrane separation unit, having two membrane modules, operating in series and under supercritical conditions.

In the case where the operating conditions are chosen in a supercritical medium (P>47 bar and T>92° C.), the feedstock upstream of the membrane is under supercritical conditions, whereas the permeate is in vapour phase. The membrane is then no longer the seat of an evaporation since, under supercritical conditions, there is no change of state when passing from the supercritical field to the vapour phase. If this situation is compared with that of pervaporation, there is therefore no longer any heat loss in the retentate induced by the vaporization of the permeate. This means that there is no longer any need for an intermediate reheater between the different membrane modules, as shown in FIGS. 6 and 6*bis*. In the same way as previously, the permeate pressure is chosen equal or close to the pressure of the distillation column, i.e. greater than or equal to 15 bar.

Generally, i.e. for all the configurations corresponding to the process according to the invention, the flow of feedstock to be treated is a $C_3$ refinery cut. This flow contains for the most part propane and propylene.

This flow can also contain impurities such as COS, H2S, mercaptans and dienes. The propylene content of such a feedstock is 60% by weight minimum.

The remainder of the description will be better understood by means of FIGS. 1 to 6 described below.

Figure 1:
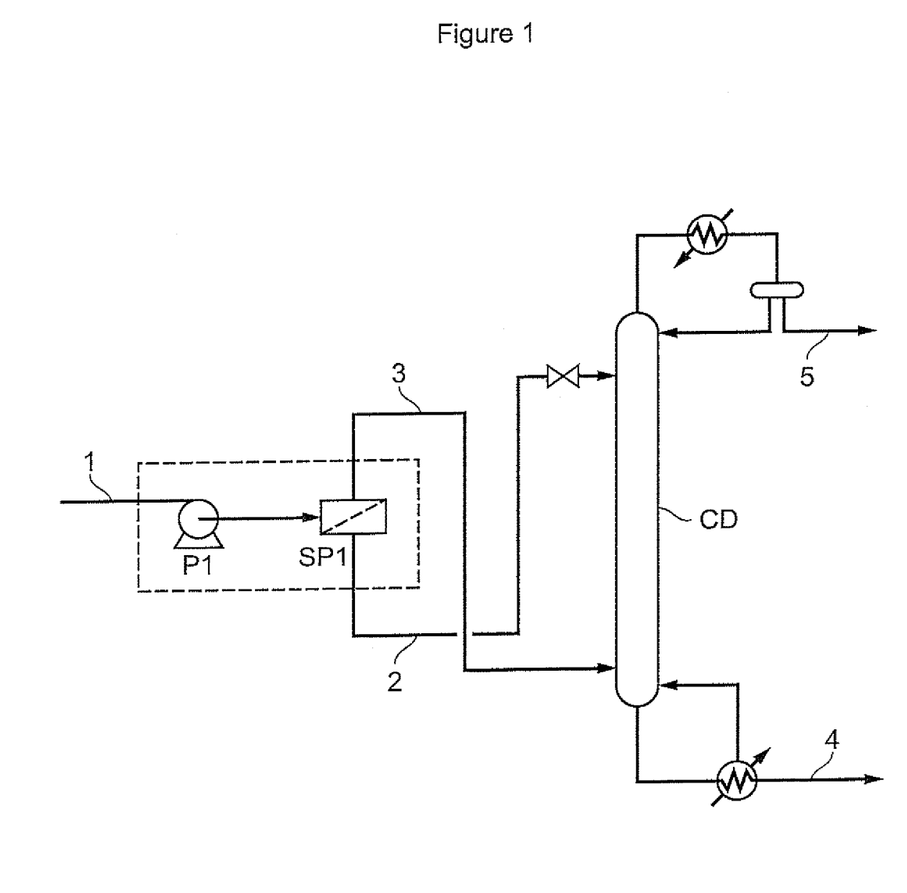
FIG. 1 shows a process diagram according to the invention, comprising a membrane separation unit situated upstream of the distillation column.

FIG. 1

The first configuration of the process, called the "upstream case" is shown diagrammatically by FIG. 1. A membrane separation unit (SP1) having one or more membrane modules placed upstream of the distillation column (CD) is used, said membrane separation unit operating under pervaporation conditions or under supercritical conditions.

The feedstock to be separated (1) is introduced into the membrane separation unit (SP1), from which a vapour permeate (2) and a liquid retentate (3) are extracted.

The vapour permeate (2) is reintroduced into the upper part of the column (CD).

The liquid retentate (3) is reintroduced into the lower part of the column (CD).

A flow (5) of high-purity polypropylene is extracted at the top of the column (CD) and a flow (4) of propane at the base of the column.

Figure 2:
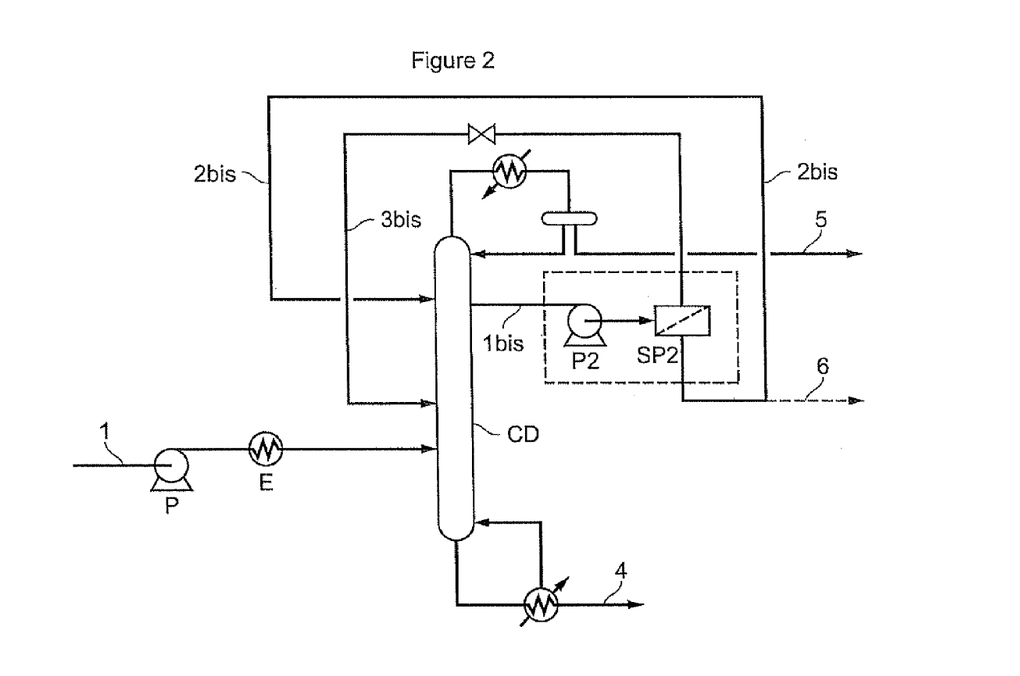
FIG. 2 shows a process diagram according to the invention, comprising a membrane separation unit situated downstream of the distillation column.

FIG. 2

The second configuration of the process according to the invention, called the "downstream case" is shown by FIG. 2. A membrane separation unit (SP2) having one or more membrane modules operating in series is used, said membrane separation unit being placed downstream of the distillation column (CD) and being able to operate under pervaporation conditions or supercritical conditions.

The feedstock to be separated (1) is introduced into the column (CD), optionally after pumping by means of a pump, and reheating by means of an exchanger (E) in order to return to pressure and temperature conditions close to those existing at the point of introduction into said column. The flow (1*a*) is drawn off from the column (CD) and is introduced into the membrane separation unit (SP2) after passing into the pump P2 in order to reach the desired pressure level. A retentate (3*a*) is extracted from the membrane separation unit (SP2), and sent into the lower part of the column (CD), and a permeate (2*a*) which is a) either reintroduced into the upper part of the column, b) or directly valorized as high-purity propylene via the flow (6).

The choice between the two possibilities a) and b) essentially depends on the draw-off point of the flow feeding the membrane separation unit (SP2).

Figure 3:
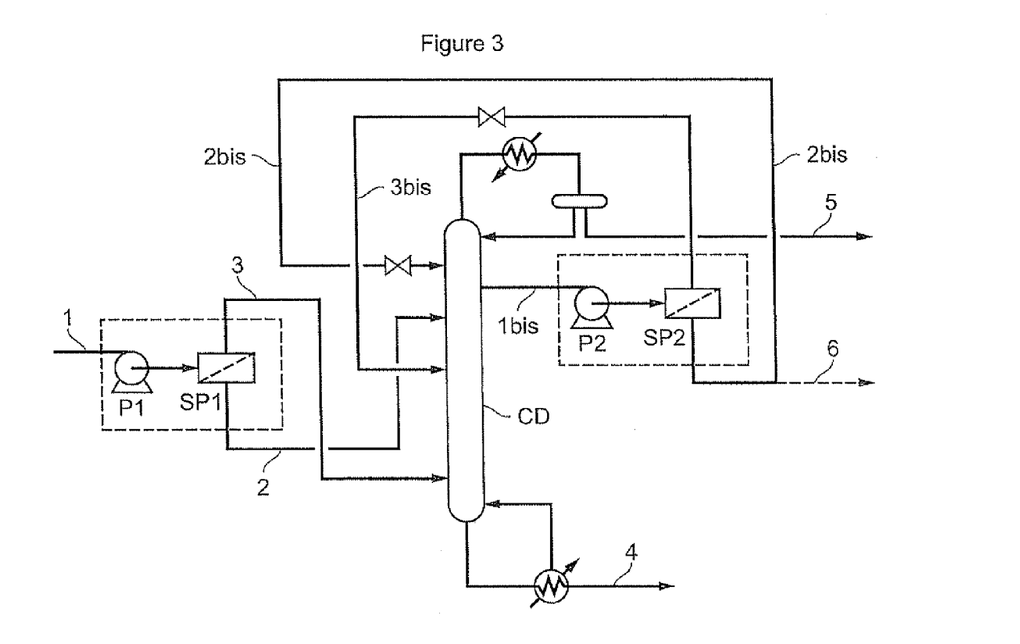
FIG. 3 shows a process diagram according to the invention, comprising both a membrane separation unit upstream of the distillation column and a membrane separation unit downstream of said column.

FIG. 3

The third configuration of the process according to the invention, the so-called "upstream+downstream" case, is shown by FIG. 3. Two membrane separation units (SP1) and (SP2) are used, one (SF1) being placed upstream, the other (SP2) being placed downstream of the column (CD).

This configuration can be described as the superimposition of the "upstream" case and the "downstream" case described above. It should be noted that in this "upstream+downstreanm" configuration, the upstream separation unit can operate under pervaporation conditions, and the downstream separation unit can operate under supercritical conditions.

Or, also, the upstream separation unit can operate under supercritical conditions and the downstream separation can operate under pervaporation conditions.

Finally, the upstream and downstream separation units can both operate under pervaporation or under supercritical conditions.

The flows having the same number in FIGS. 1, 2 and 3 correspond to identical flows.

Figure 4:
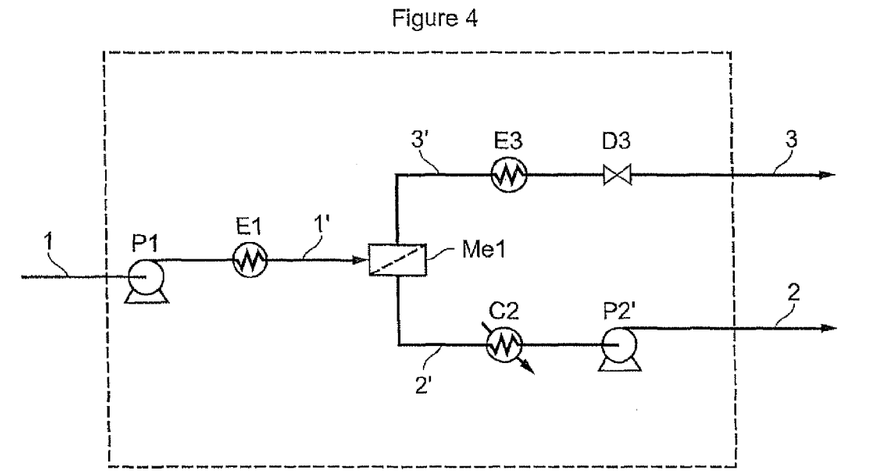
FIG. 4 shows a membrane separation unit, having a single membrane module, and operating under pervaporation conditions.

FIGS. 4 and 4*bis*

FIGS. 4 and 4*bis* represent a separation unit having a single membrane module (Me1), said separation unit being able to be placed upstream or downstream of the column (CD not shown in FIGS. 4 and 4*bis*).

The feedstock to be treated (1) is pumped by means of the pump P1, then reheated by means of the exchanger (E1) to a temperature approaching, to within 10° C., the bubble temperature of the feedstock at the pressure upstream of the membrane module (Me1). The feedstock (1) becoming (1') is then introduced into the membrane module (Me1) from which a retentate (3') and a permeate (2') are extracted.

The permeate (2') becoming (2) is:

a) either condensed in the condenser (C2), then pumped into the pump (P2'), then reintroduced into the distillation column (CD) as shown in FIG. 4, b) or reintroduced directly into the column (CD) as shown in FIG. 4*bis*.

The liquid retentate (3') becoming (3) is reintroduced at the base of the distillation column (CD) after cooling in the exchanger (E3) and pressure reduction in the pressure-reducing valve (D3).

The description remains the same, whether the membrane module operates under pervaporation conditions or under supercritical conditions.

FIGS. 5 and 5*bis*

FIGS. 5 and 5*bis* show the case where the separation unit has two membrane modules operating under pervaporation conditions.

The feedstock to be treated (1) is pumped by means of the pump P1 then reheated by means of the exchanger (E1) to a temperature approaching, to within 10° C., the bubble temperature of the feedstock at the pressure upstream of the membrane module (Me1). The feedstock (1) is then introduced into the first membrane module (Me1) from which a retentate (3') and a permeate (2') are extracted.

The liquid retentate (3') from the first membrane module (Me1) passes through an exchanger (E2) in order to be reheated to a temperature approaching, to within 10° C., the bubble temperature of this retentate, and is then reintroduced into the second membrane module (Me2).

The permeate (2") from the second membrane module (Me2) is then added to the permeate (2') from the first membrane module (Me1) by means of the mixer (M1). The permeate (2") is:

a) either condensed in the condenser (C2) and reintroduced into the distillation column (CD), not shown in FIGS. 5 and 5*bis*, via the flow (2) after passing into a pump (P2') as shown in FIG. 5, b) or reintroduced directly into the column (CD) via the flow (2) as shown in FIG. 5*bis*.

The liquid retentate (3") from the second membrane module (Me2) is reintroduced at the base of the distillation column (CD) in the form of the flow (3) after cooling in the exchanger (E3) and pressure reduction in the pressure-reducing valve (D3).

The description is the same whether the membrane unit is placed upstream or downstream of the column (CD).

FIGS. 6 and 6*bis*

FIGS. 6 and 6*bis* show the case where the separation unit has two membrane modules operating under supercritical conditions.

The feedstock to be treated (1) is pumped by means of the pump P1 then reheated by means of the exchanger (E1) to a temperature above 92° C.

The feedstock (1) is then introduced into the first membrane module (Me1) from which a liquid retentate (3') and a vapour permeate (2') are extracted.

The liquid retentate (3') from the first membrane module (Me1) is reintroduced directly into the second membrane module (Me2).

The permeate (2") becoming (2), from the second membrane module (Me2) is then added to the permeate (2') from the first membrane module (Me1) by means of the mixer (M1). The permeate (2") is:

a) either condensed in the condenser (C2) and reintroduced into the distillation column (CD), not shown in FIGS. 6 and 6*bis*, via the flow (2), after passing into a pump (P2) as shown in FIG. 6, b) or reintroduced directly into the column (CD) via the flow (2) as shown in FIG. 6*bis*. The liquid retentate (3") becoming (3), from the second membrane module (Me2) is reintroduced at the base of the distillation column (CD) after cooling in the exchanger (E3) and pressure reduction in the pressure-reducing valve (D3).

EXAMPLES

The following three examples illustrate the benefit of the invention in terms of economic profitability and increase in production capacity.

The first 2 examples are in the form of a comparison between 3 systems according to the invention (denoted "upstream" case/"downstream" case/"upstream-1-downstream" case) and a base case corresponding to the prior art and having only one distillation column (with no membrane separation unit). The third example according to the invention compares the pervaporation and supercritical operating conditions.

In all the examples according to the invention, a polymer membrane is used with permeability equal to 10 barrer and propylene/propane selectivity equal to 10.

Example No. 1

Comparison of the Performances of the Process according to the Invention/Prior Art under "Pervaporation Conditions"

This example makes it possible to evaluate the saving that can be made by integrating the membrane separation units with the propylene/propane distillation column with a view to treating the same feedstock capacity.

Base Case (Prior Art)

The base case consists of a separation of a propylene/propane feedstock carried out by means of a distillation column comprising 170 plates and operating with a reflux rate of 13.

TABLE 1

| Characteristics of the propylene/propane distillation column used for the base case | |
| --- | --- |
| Temperature at top | 49.1° C. |
| Temperature at base | 65.8° C. |
| Pressure at top | 20.5 bar |
| Theoretical plates | 168 + condenser & reboiler |
| Feed | liquid at plate 121 |
| Draw-off at top | 99.5% by mass of propylene |
| Draw-off at base | 5% by mass of propylene |
| ΔP | 0.01 bar/plate |

The main operating cost of the distillation column is to be found in the heat to be supplied to the reboiler and to the condenser.

Table 2 below gives the composition of the feedstock to be treated, the operating conditions and the specifications relating to the products fixed as objectives.

TABLE 2

| Material balance in the base case | | | | |
| --- | --- | --- | --- | --- |
| Description of the flows | | FEEDSTOCK | PROPANE | PROPYLENE |
| Phase | | Liquid | Liquid | Liquid |
| Pressure | bar | 25.38 | 22 | 20.1 |
| Temperature | ° C. | 63.1 | 69 | 49 |
| Mass flow rate | kg/h | 16699.8 | 4651.3 | 12048.5 |
| PROPENE | % by mass | 73 | 5 | 99.5 |
| PROPANE | % by mass | 20 | 72 | 0.5 |
| BUTANE | % by mass | 7 | 23 | 0.0 |

Table 3 gives the heat exchanged in the reboiler and the condenser of the distilation column for the base case.

TABLE 3

| Heat in the condenser and the reboiler in the distillation column in the base case. | |
| --- | --- |
| Apparatus | Heat exchanged (MW) |
| Condenser | 18.3 |
| Reboiler (type BKT) | 18.2 |

Upstream Case (According to the Invention)

FIG. 1 shows the diagram of the process according to the invention according to the upstream case in which the separation unit (SPI) is placed upstream of the column (CD).

The feedstock is initially pumped and reheated by the pump (P1) and the exchanger (E1).

The separation unit (SPI) operates under pervaporation conditions.

The separation unit (SPI) with a module (Me1) is described in FIG. 4.

The feedstock is raised to 40 bar and 83° C. (4° C. below the bubble point).

The pressure difference through the membrane is a parameter to be defined according to two possibilities:

ΔP=20 bar, the permeate is at the same pressure as the injection plate, which makes it possible to reinject the permeate directly into the column. This is not the choice made in this example.

ΔP=25 bar (configuration chosen in this example), the difference in pressure is maximized in order to obtain greater separation effectiveness. The permeate is then at a pressure lower than that in the column, a condenser is thus placed on the permeate flow followed by a pump in front of the reinjector (here $T_{condensation}$=33° C., using a water-cooled condenser).

The permeate [2] is reintroduced between plates 1 and 85, specifically in this example at plate 76.

The retentate [3] is reintroduced between plates 170 and 86, specifically in this example at plate 133.

The operating conditions chosen for the example are as follows:

TABLE 4

Configuration used to calculate the "upstream case" example

| | |
|---|---|
| $P_{feedstock}$ | 40 bar |
| $T_{feedstock}$ | 83.2° C. |
| ΔP | 25 bar |
| Separation unit | an upstream separation unit including a membrane module (cf. FIG. 4) |
| reinjection of the permeate into the column | after condensation at 33° C. |

Table 5 below gives the material balance around the separation unit

TABLE 5

Material balance on the membrane placed upstream of the distillation column

| | | Name of the flow | | |
|---|---|---|---|---|
| | | FEEDSTOCK | PERMEATE | RETENTATE |
| | | | Description | |
| | | [1] | [2] | [3] |
| Pressure | bar | 39.5 | 15 | 39 |
| Temperature | ° C. | 83.2 | 67.2 | 67.2 |
| Total mass rate | kg/h | 19300.00 | 6101.48 | 13198.52 |
| ETHANE | % by | 0.000 | 0.001 | 0.000 |
| PROPENE | weight | 0.732 | 0.944 | 0.634 |
| PROPANE | | 0.204 | 0.055 | 0.272 |
| BUTANE | | 0.061 | 0.000 | 0.089 |
| 12BD | | 0.003 | 0.000 | 0.005 |

Downstream Case (According to the Invention)

FIG. 2 shows a diagram of the process according to the invention according to the downstream case in which the separation unit (SP2) is placed downstream of the column (CD). As shown in FIG. 2, the permeate (2) can either be reinjected into the column via the flow (2a), or leave the process, via the flow (6), in the case where it already has the specified purity.

The feedstock to be treated is drawn off at a plate such that the composition of the feedstock is superior to the composition on entering the process, then the feedstock is pumped and reheated by means of the pump (P1) and the exchanger (E1).

The liquid (1') is drawn off from the column at plate 70.

The drawn-off liquid (1) is injected into the membrane separation unit (SP2) at a pressure and temperature close to the critical point.

At the outlet from the downstream membrane separation unit (SP2), the permeate (2) is reinjected into the column (flow 2a), at plate 28, and the retentate (3) is reintroduced at plate 83.

The possible configurations for the separation unit (SP2) with one module are described in FIG. 4 and FIG. 4bis.

The operating conditions chosen for the example are as follows:

TABLE 6

Configuration used to calculate the "downstream case" example

| | |
|---|---|
| $P_{feedstock}$ | 40 bar |
| $T_{feedstock}$ | 79.4° C. |
| ΔP | 25 bar |
| Separation unit | separation unit including a membrane module |
| reinjection of the permeate into the column | after condensation at 35° C. (water-cooled condenser) |

Table 7 below gives the material balance around the separation unit

TABLE 7

Material balance on the membrane placed downstream of the distillation column

| | | Name of the flow | | |
|---|---|---|---|---|
| | | FEEDSTOCK | PERMEATE | RETENTATE |
| | | | Description | |
| | | [1] | [2] | [3] |
| Pressure | bar | 39.5 | 15 | 39 |
| Temperature | ° C. | 79.4 | 52.4 | 52.4 |
| Flow rates | kg/h | 13000.00 | 4694.5 | 8305.5 |
| ETHANE | % by | 0.00 | 0.00 | 0.00 |
| PROPENE | mass | 0.89 | 0.99 | 0.84 |
| PROPANE | | 0.11 | 0.01 | 0.16 |
| BUTANE | | 0.00 | 0.00 | 0.00 |

Upstream+Downstream Case (According to the Invention)

FIG. 3 shows a diagram of the process according to the invention in the "upstream+downstream" case which uses 2 membrane units, SP1 placed upstream of the distillation column (CD) and SP2 placed downstream of said column.

The downstream membrane separation unit (SP1) operates under the same conditions as in the "downstream" case.

The upstream membrane separation unit (SP2) operates under the same conditions as in the "upstream" case.

The operating conditions are given in Table 8 below.

TABLE 8

Configuration used to calculate the "upstream + downstream" case example

| | Upstream unit (M1) | Downstream unit (M2) |
|---|---|---|
| $P_{feedstock}$ | 40 bar | 40 bar |
| $T_{feedstock}$ | 83.2° C. | 79.4° C. |
| ΔP | 25 bar | 25 bar |
| Separation unit | an upstream separation unit including a membrane module (cf. FIG. 4) | a downstream separation unit including two membrane modules (cf. FIG. 5) |
| reinjection of the permeate into the column | after condensation at 35° C. (water-cooled condenser) | after condensation at 35° C. (water-cooled condenser) |

The three "upstream"/"downstream"/"upstream+downstream" cases were compared by simulation by means of the commercial software PROII for the same flow rate of feedstock to be separated. The processes according to the invention ""upstream"/"downstream"/"upstream+downstream") allow a reduction in the heat exchanged in the reboiler of the column of up to 20% for the "upstream+downstream" case.

Table 9 below shows the results of this comparison.

TABLE 9

Evaluation of the energy saving for the 3 proposed systems

|  | Reference case | "Upstream" case | "Downstream" Case | "Upstream + downstream" case |
|---|---|---|---|---|
| Feedstock flow rate (kg/h) |  | 16,700 |  |  |
| Q reboiler (MW) | 18.2 | 16.3 | 16.3 | 14.5 |
| % reduction/ base case | — | 10.4% | 10.4% | 20.3% |

Example No. 2

Illustrating the Increase in the Capacity of the Distillation Column Under "Pervaporation Conditions"

The process according to the invention makes it possible to increase the treatment capacity of the installed distillation column.

Simulations carried out on the commercial software (PROII) have made it possible to define the new flooding limits of the distillation column in the process according to the invention and thus to reach the maximum treatment capacity of the process according to the invention.

The calculations showed a treatment capacity up to 37% greater than the reference case for the "upstream+downstream" case.

The process according to the invention in the "upstream+downstream" case is of particularly great benefit within the framework of a debottlenecking of the gas plant.

The reduction in the manufacturing cost for this configuration is assessed at up to 17% compared with the reference case, as shown by Table 10 below.

TABLE 10

Evaluation of the propylene separation cost for the "upstream" case and the "upstream + downstream" case.

|  | Reference case | Upstream case (*) | Upstream + Downstream case (*) |
|---|---|---|---|
| feedstock flow rate (kg/h) | 16,700 | 19,300 | 22,900 |
| additional column capacity |  | 16% | 37% |
| Manufacturing cost/tonne of PG propylene (€/tonne)* | 34.3 | 30.8 | 28.2 |
| Manufacturing cost saving/reference |  | 10% | 17.6% |

*calculated with the costs of utilities in Europe in 2006

Example No. 3

Comparison of the Pervaporation Conditions and Supercritical Conditions (According to the Invention)

A comparison was carried out between the pervaporation conditions and the supercritical conditions for the upstream case according to the invention (according to FIG. 1) using an upstream separation unit, itself constituted by 2 membrane modules in series.

The upstream case operating under pervaporation conditions corresponds to FIGS. 5 and 5bis, and the upstream case operating under supercritical conditions corresponds to FIGS. 6 and 6bis.

Operation under supercritical conditions makes it possible to avoid vaporization through the membrane, thus making the intermediate reheater unnecessary (denoted E2 in FIG. 5).

As regards the supercritical case, we have here calculated the two options for reinjection of the permeate.

permeate condensed, pumped and recycled in liquid form into the column (supercritical upstream case 1 according to FIG. 6)
  permeate injected directly into the column (supercritical upstream case 2 according to FIG. 6bis).

TABLE 11

Configurations used for the examples comparing industrial conditions and supercritical conditions.

|  | Supercritical upstream case 1 | Supercritical upstream case 2 | Pervaporation upstream case |
|---|---|---|---|
| $P_{feedstock}$ | 50 bar | 50 bar | 40 bar |
| $T_{feedstock}$ | 95° C. | 95° C. | 83° C. |
| ΔP membrane module | 25 bar (permeate 20 bar) | 30 bar (permeate 15 bar) | 25 bar |
| Separation unit | an upstream separation unit including two membrane modules (cf. FIG. 6) | an upstream separation unit including two membrane modules (cf. FIG. 6bis) | an upstream separation unit including two membrane modules (cf. FIG. 5) |
| reinjection of the permeate into the column | condensation at 50° C. (cooling tower) | reinjection directly into the column (no condensation) | condensation at 30° C. (water-cooled condenser) |

The feedstock flow (1) is raised to a pressure above the critical point (P>50 bar), which makes it possible to have permeate at a pressure of approximately 25 bar (keeping the same pressure difference ΔP when passing through the membrane). Therefore, the permeate is at a higher pressure and can be condensed with an air-cooled condenser, denoted (C2) in FIG. 6, with a lower utilities requirement than a water-cooled condenser such as that of the case of operation under pervaporation conditions.

In order to determine the advantage of the supercritical regime, a utilities balance was prepared for operation under pervaporation conditions and operation under supercritical conditions. Table 12 below gives the results.

TABLE 12

Comparison of the pervaporation and supercritical regimes, and impact on the cost of propylene separation

|  | Reference case | Pervaporation regime | Supercritical regime 1 | Supercritical regime 2 |
|---|---|---|---|---|
| product manufacturing cost (euros/tonne) | 34.3 | 31.3 | 30 | 30.2 |
| reduction in manufacturing costs/reference case |  | 8.7% | 12.5% | 12.0% |

The use of the supercritical conditions in an "upstream" system with a separation unit using two membrane modules allows a reduction in the manufacturing costs of approximately 12% compared with the reference case.

The invention claimed is:

1. A process comprising separating propane and propylene in a distillation column and at least one separation unit constituted by several membrane modules operating in series, said separation unit or units being placed either upstream, or downstream, or upstream and downstream of the distillation column, said membrane module or modules comprises polymer membranes having a propylene permeability greater than 0.1 barrer and propylene/propane selectivity greater than 5, said membrane module or modules operating under the following pervaporation conditions provided at the inlet to each membrane module: feedstock pressure comprised between 20 and 47 bar and feedstock temperature between 20° C. and 92° C., said separation unit or units operating with a difference in pressure such that a permeate is at a minimum pressure of 10 bar and
wherein the permeate is reinjected either upstream, or downstream, or upstream and downstream of the distillation column in vapour phase.

2. The process of claim 1 wherein the permeate is directly obtained as high-purity propylene without a further distillation step.

3. The process of claim 1 in which the pressure of the permeate is equal to or greater than the pressure of the distillation column.

4. A process comprising separating propane and propylene in a distillation column and at least one separation unit constituted by several membrane modules operating in series, said separation unit or units being placed either upstream, or downstream, or upstream and downstream of the distillation column, said membrane module or modules provided with polymer membranes with propylene permeability greater than 0.1 barrer and propylene/propane selectivity greater than 5, said module or modules operating under the following supercritical conditions, provided at the inlet to each membrane module: feedstock pressure comprised between 47 and 100 bar and feedstock temperature between 92° C. and 200° C., said separation unit or units operating with a difference in pressure such that the permeate is at a minimum pressure of 10 bar and
wherein the permeate is reinjected either upstream, or downstream, or upstream and downstream of the distillation column in vapour phase.

5. The process of claim 4 further comprising steps wherein the permeate is condensed, repumped and reintroduced in liquid phase into the column.

6. The process for separating propane and propylene according to claim 4 in which the permeate is valorized as high-purity polymer-grade propylene for polymerization processes.

7. The process of claim 4 in which the pressure of the permeate is equal to or greater than the pressure of the distillation column.

* * * * *